United States Patent [19]  [11] 4,283,532
Nohara  [45] Aug. 11, 1981

[54] PROCESS FOR PREPARATION OF O-(2,6-DICHLOROANILINO)PHENYLACETIC ACID AND NOVEL INTERMEDIATE FOR USE IN PREPARATION OF THE SAME

[75] Inventor: Fujio Nohara, Kamiichi, Japan

[73] Assignee: Ikeda Mohando Co., Ltd., Toyama, Japan

[21] Appl. No.: 64,404

[22] Filed: Aug. 7, 1979

[30] Foreign Application Priority Data

Aug. 8, 1978 [JP] Japan ................... 53-96434

[51] Int. Cl.$^3$ .................... C07C 51/06; C07C 102/00; C07D 295/18
[52] U.S. Cl. .................... 544/165; 564/163; 564/168; 562/456; 546/226; 544/391; 260/326.5 E; 260/544 D
[58] Field of Search .................... 562/454, 456, 457; 564/163, 168; 544/165, 391; 546/226; 260/326.5 E

[56] References Cited

U.S. PATENT DOCUMENTS

| | | | |
|---|---|---|---|
| 2,553,914 | 5/1951 | Goldberg | 562/456 |
| 3,390,172 | 6/1968 | Schever | 562/456 |
| 3,590,039 | 6/1971 | Sallmann et al. | 562/456 |

FOREIGN PATENT DOCUMENTS

| | | |
|---|---|---|
| 53-7640 | of 1978 | Japan . |
| 34-27374 | of 1959 | Japan . |
| 45-11295 | of 1970 | Japan . |
| 46-43977 | of 1946 | Japan . |
| 51-4078 | of 1976 | Japan . |
| 52-71439 | of 1977 | Japan . |

OTHER PUBLICATIONS

Folia Pharmacologica Japanica, vol. 69, pp. 299–318, (1973).
MeOmie, "Protective Groups in Organic Chemistry," p. 191, (1974).
Alhede et al., Chem. Abst., vol. 72, p. 305, #12408p (1970).
Morris et al., Organic Chem., pp. 670–671, (1966).

*Primary Examiner*—Natalie Trousof
*Assistant Examiner*—James H. Reamer

[57] ABSTRACT

Disclosed is a process for the preparation of o-(2,6-dichloroanilino)phenylacetic acid (Diclofenac) or its pharmacologically acceptable acid addition salt, which comprises hydrolyzing an N,N-disubstituted-o-(2,6-dichloroanilino)phenylacetamide derivative with an alkali. Also a novel intermediate for use in the preparation of Diclofenac, that is, an N,N-disubstituted-o-halogenophenylacetamide in which the halogen is iodine or bromine, is disclosed.

2 Claims, No Drawings

PROCESS FOR PREPARATION OF O-(2,6-DICHLOROANILINO)PHENYLACETIC ACID AND NOVEL INTERMEDIATE FOR USE IN PREPARATION OF THE SAME

BACKGROUND OF THE INVENTION (1) Field of the Invention

The present invention relates to a process for the preparation of o-(2,6-dichloroanilino)phenylacetic acid represented by the following formula (III):

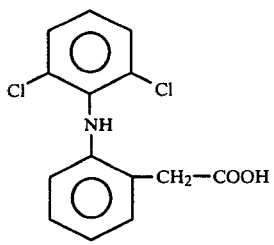

(III)

which is broadly used under the general name of "Diclofenac" as a non-steroidal analgesic anti-inflammatory agent, and its pharmacologically acceptable acid addition salt, and also to a novel intermediate for use in the preparation of Diclofenac, which is represented by the following general formula (I):

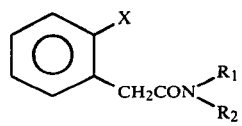

(I)

where $R_1$ and $R_2$, which may be the same or different, stand for a lower alkyl group, or one of $R_1$ and $R_2$ stands for a lower alkyl group and the other of $R_1$ and $R_2$ stands for a phenyl or benzyl group, or $R_1$ and $R_2$ are bonded together to form a heterocyclic ring together with a nitrogen atom and/or and oxygen atom; and X stands for an iodine or bromine atom.

(2) Description of the Prior Art

Various processes for the preparation of o-(2,6-dichloroanilino)phenylacetic acid have been proposed. Some of them are described below.

(a) Japanese Patent Publication No. 27374/59 (British Pat. No. 1,139,332, Ciba-Geigy) discloses a process comprising hydrolyzing a nitrile represented by the following formula:

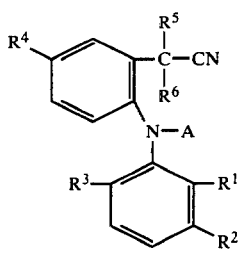

with an alkali metal hydroxide in an aqueous medium at the boiling point thereof form a compound represented by the following formula:

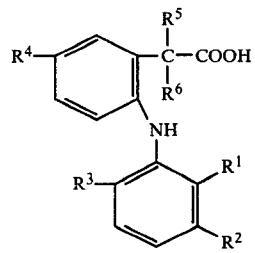

In the foregoing formulae, $R^1$ stands for a hydrogen or halogen atom or an alkyl group, $R^2$ stands for a hydrogen or halogen atom or an alkyl or trifluoromethyl group, $R^3$ stands for a hydrogen or halogen atom or an alkyl group, with the proviso that the case where all of $R^1$, $R^2$ and $R^3$ stand for a hydrogen atom is excluded, $R^4$ stands for a hydrogen or halogen atom or an alkyl group, $R^5$ stands for a hydrogen atom or an alkyl group, $R^6$ stands for a hydrogen atom and A stands for a hydrogen atom or an acyl group, particularly an alkanoyl group.

(b) Japanese Patent Publication No. 11295/70 (Ciba-Geigy) discloses a process comprising hydrolyzing an ester represented by the following formula:

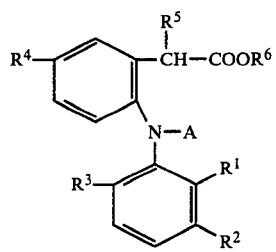

with an alkali metal hydroxide, an alkali metal carbonate or an alkali metal bicarbonate in the presence of a basic ion exchanger to form a compound represented by the following formula:

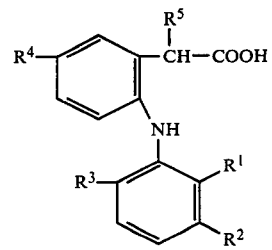

In the foregoing formulae, $R^1$ stands for a hydrogen or halogen atom or an alkyl group, $R^2$ stands for a hydrogen or halogen atom or a alkyl or trifluoromethyl group, $R^3$ stands for a hydrogen or halogen atom or an alkyl or alkoxy group, with the proviso that the case where all of $R^1$, $R^2$ and $R^3$ stand for a hydrogen atom is excluded, $R^4$ stands for a hydrogen or halogen atom, $R^5$ stands for a hydrogen atom or an alkyl group, $R^6$ stands for an alkyl or aralkyl group, particularly a benzyl group, and A stands for an acyl group, particularly an alkanoyl group.

(c) Japanese Patent Application Laid-Open Specification No. 71439/77 (Nippon Chemiphar Co., Ltd.) discloses a process comprising reacting a compound represented by the following formula:

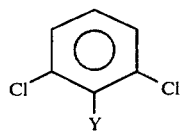

with a compound represented by the following formula:

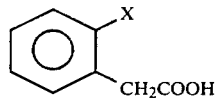

in the presence of a copper catalyst in a solvent to obtain a compound of the following formula:

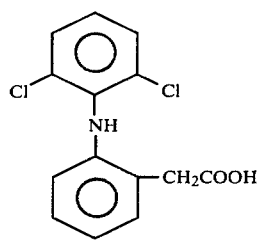

in a yield of 13 to 18%.

In the foregoing formulae, Y stands for a halogen atom or an amino group and X stands for an amino group or a halogen atom.

(d) Japanese Patent Application Laid-Open Specification No. 7640/78 (Teikoku Hormone Mfg. Co., Ltd.) discloses a process comprising reacting a compound of the following formula:

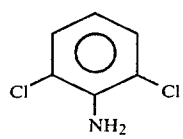

with a compound of the following formula:

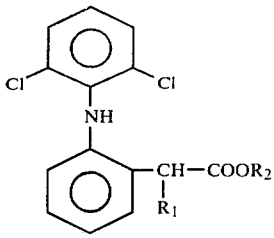

in the presence of a copper catalyst in a solvent to form a compound of the following formula:

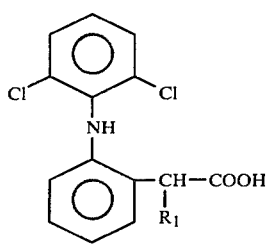

in a yield of 40 to 83%, and if necessary, saponifying the so obtained compound under alkaline conditions to obtain a compound represented by the following formula:

In the foregoing formulae, $R_1$ stands for a hydrogen atom or a methyl group, and $R_2$ stands for a methyl, propyl or a t-butyl group.

All of these known processes, however, are industrially insufficient and defective because the number of steps to Diclofenac is very large and the yield is extremely low at one or more of these many steps.

BRIEF SUMMARY OF THE INVENTION

In accordance with the present invention, there is provided an industrial process for the preparation of o-(2,6-dichloroanilino)phenylacetic acid or its pharmacologically acceptable acid addition salt, which comprises hydrolyzing an N,N-dialkyl-o-(2,6-dichloroanilino)phenylacetamide derivative, N,N-monoalkyl-monophenyl-o-(2,6-dichloroanilino)-phenylacetamide derivative, N,N-monoalkyl-monobenzyl-o-(2,6-dichloroanilino)phenylacetamide derivative or N,N-di-heterocyclic-o-(2,6-dichloroanilino)-phenylacetamide derivative (hereinafter referred to as "N,N-disubstituted-o-(2,6-dichloroanilino)phenylacetamide derivative") represented by the following general formula (II):

(II)

wherein $R_1$ and $R_2$, which may be the same or different, stand for a lower alkyl group, or one of $R_1$ and $R_2$ stands for a lower alkyl group and the other of $R_1$ and $R_2$ stands for a phenyl or benzyl group, or $R_1$ and $R_2$ are bonded together to form a heterocyclic ring together with a nitrogen atom and/or an oxygen atom, with an alkali.

In accordance with the present invention, there is also provided a process for the preparation of o-(2,6-dichloroanilino)phenylacetic acid or its pharmacologically acceptable acid addition salt, which comprises reacting a compound represented by the following general formula (I):

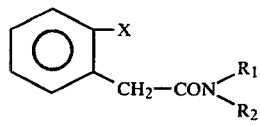
(I)

wherein $R_1$ and $R_2$ are as defined above and X stands for an iodine or bromine atom, with 2,6-dichloroaniline in the presence of a copper catalyst to form an N,N-disubstituted-o-(2,6-dichloroanilino)phenylacetamide derivative represented by the following general formula (II):

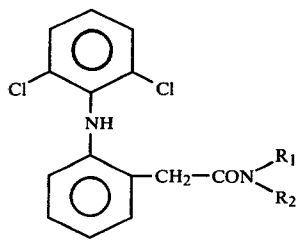
(II)

wherein $R_1$ and $R_2$ are as defined above, and hydrolyzing the so obtained compound with an alkali.

Furthermore, in accordance with the present invention, there is provided a process for the preparation of o-(2,6-dichloroanilino)phenylacetic acid or its pharmacologically acceptable acid addition salt, which comprises reacting a compound represented by the following general formula (I):

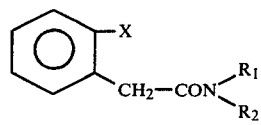
(I)

wherein $R_1$, $R_2$ and X are as defined above, in the presence of a copper catalyst with a compound obtained by reacting 2,6-dichloroaniline with an alkali metal hydride to form an N,N-disubstituted-o-(2,6-dichloroanilino)phenylacetamide derivative represented by the following general formula (II):

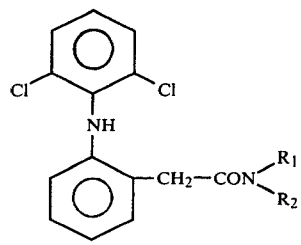
(II)

wherein $R_1$ and $R_2$ are as defined above, and hydrolyzing the so obtained compound with an alkali.

A compound represented by the general formula (I) is a novel compound. Accordingly, the present invention provides a novel compound valuable as the starting compound to be used for the preparation of Diclofenac.

More specifically, in accordance with the present invention, there is provided a process for the preparation of novel compounds represented by the following general formula (I):

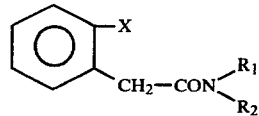
(I)

wherein $R_1$, $R_2$ and X are as defined above. which comprises (A) reacting o-iodophenylacetic acid or o-bromophenylacetic acid with thionyl chloride to form an acid chloride and reacting the so obtained acid chloride, as it is or after removal of the unreacted thionyl chloride, with an amine compound represented by the following general formula (V):

(V)

wherein $R_1$ and $R_2$ are as defined above, (B) reacting an N,N-disubstituted-phenylacetamide derivative represented by the following general formula (IV):

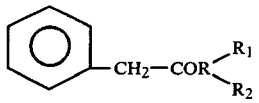
(IV)

wherein $R_1$ and $R_2$ are as defined above, with a halogen, particularly bromine or iodine, or (C) reducing a compound represented by the following general formula (VII):

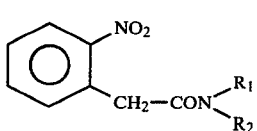
(VII)

wherein $R_1$ and $R_2$ are as defined above, to form a corresponding amino compound, diazotizing the so formed amino compound with nitrous acid and reacting the diazotized compound with potassium iodide or potassium bromide.

DETAILED DESCRIPTION OF THE PREFERRED EMBODIMENTS

The present invention relates to a novel process for the preparation of o-(2,6-dichloroanilino) phenylacetic acid (Diclofenac) or its pharmacologically accetable acid addition salt and also to a process for the preparation of a novel N,N-disubstituted o-halogenophenylacetamide derivative which is valuable as the starting compound to be used in the first-mentioned process.

The process of the present invention can be represented by the following chemical formulae:

(First Step)

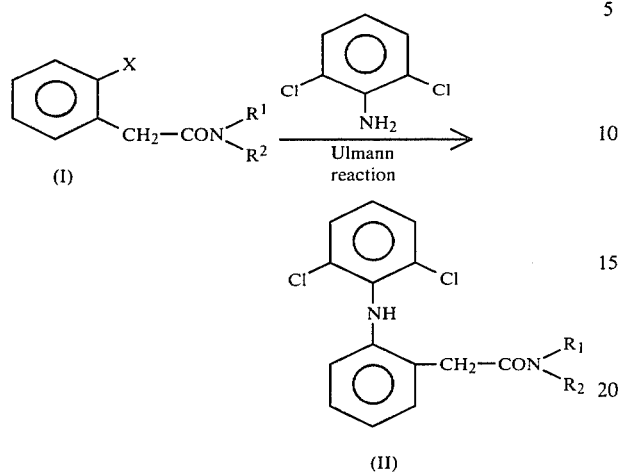

(Second Step)

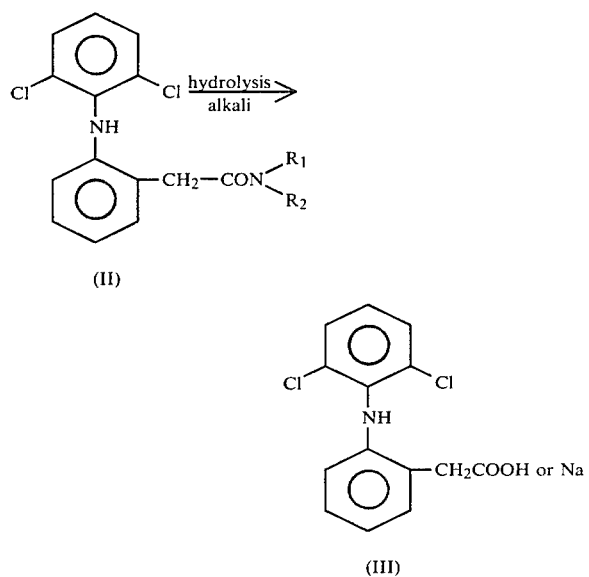

The above two steps will now be described.

(1) First Step:

In the first step, an N,N-disubstituted-o-halogenophenylacetamide of the formula (I) is condensed with 2,6-dichloroaniline to form as an intermediate an N,N-disubstituted-o-(2,6-dichloroanilino)phenylacetamide derivative of the formula (II).

It is known that a diphenylamine can be prepared by Ulmann reaction. Accordingly, it may be said that the first step is a process for preparing a valuable intermediate according to Ulmann reaction in a broad sense. The compound of the formula (I) that is used as one starting compound is a novel compound, and this compound may be prepared, for example, according to processes (A), (B) and (C) described hereinafter.

A copper catalyst is used at this first step. For example, a powder or porous product obtained by chemically or physically treating copper or a copper-containing alloy, or a copper salt such as copper halide, copper acetate, copper oxide or copper sulfate can be used as the copper catalyst. Cuprous bromide, cuprous iodide and copper powder are especially preferred. The copper catalyst is ordinarily used in an amount of 5 to 50% by weight based on the amide derivative of the formula (I).

When an inorganic iodide such as sodium iodide or potassium iodide is used as an assistant or promotor in combination with the copper catalyst for the reaction of the first step, the reaction is advanced very smoothly. Furthermore, the reaction is accelerated when an acid binder, for example, an inorganic salt such as an alkali metal carbonate, is used. The use of granular or finely divided potassium carbonate is especially preferred. Ordinarily, good results are obtained if such acid binder is used in an amount sufficient to neutralize the acid formed by the reaction. Of course, the acid binder may be used in an excessive amount.

In the reaction of the first step, 2,6-dichloroaniline is used in an amount of 1 to 5 moles per mole of the N,N-disubstituted-o-halogenophenylacetamide derivative of the formula (I). Even when 2,6-dichloroaniline is used in a molar excess, the unreacted 2,6-dichloroaniline can easily be recovered.

The other starting compound to be used in the reaction of the first step, that is, 2,6-dichloroaniline, is easily available at the market and a commercially available product can be used as it is.

According to another embodiment of the first step, 2,6-dichloroaniline is first reacted with an alkali metal hydride to form an alkali metal salt of 2,6-dichloroaniline, and this alkali metal salt is used as the starting compound and is reacted with the N,N-disubstituted-o-halogenophenylacetamide derivative of the formula (I). It has been found that this embodiment is advantageous in that the condensing reaction is completed within a relatively short time and an acid binder need not be used.

When the acetamide derivative of the formula (I) is condensed with 2,6-dichloroaniline according to the first-mentioned embodiment, the reaction is advanced while the acid formed by the reaction is neutralized by the acid binder. Accordingly, water is formed in an equimolar amount by this neutralization reaction. On the other hand, in the present embodiment using an alkali metal salt of 2,6-dichloroaniline as the starting compound, only an alkali metal iodide or bromide is formed by the reaction and water is not formed at all. Accordingly, the above-mentioned advantages can be attained.

The use of a solvent is not particularly critical in the reaction of the first step. However, in order to maintain a constant reaction temperature, an inert organic solvent may be used in an allowable amount, that is, 10 to 50 moles per mole of the acetamide derivative of the formula (I). For example, there may be employed chlorobenzene, bromobenzene, dichlorobenzene, toluene, xylene, nitrobenzene and dimethyl formamide.

The reaction is carried out at a temperature higher than about 80° C., and a temperature of from about 100° C. to about 200° C. is most preferred.

The reaction is ordinarily conducted for about 1 to about 300 hours. Of course, in the present invention, the reaction time is not limited within this range.

At the first step of the present invention, side reactions are hardly caused to occur and the compound of the formula (II) can be obtained substantially quantitatively.

In constrast, if the N,N-disubstituted-o-halogenophenylacetamide derivative of the formula (I) is replaced by a corresponding o-halogenophenylacetic acid, the condensation is not caused at all.

As is seen from the chemical formula (I), the o-halogenophenylacetamide derivative of the formula (I) that is used in the present invention has a terminal side chain structure of an acid amide of a secondary amine, that is, a tertiary amide. When the terminal side chain structure is of the type other than the secondary amine acid amine, for example, in case of a compound of the general formula (I) where one of $R_1$ and $R_2$ is a hydrogen atom and the other of $R_1$ and $R_2$ is a substituted phenyl, an intramolecular cyclization takes place.

Furthermore, when o-iodo-benzylnitrile or o-bromo-benzylnitrile is used instead of the N,N-disubstituted-o-halogenophenylacetamide derivative of the formula (I) specified in the present invention and condensed with 2,6-dichloroaniline, corresponding o-(2,6-dichloroanilino)benzylnitrile represented by the following formula:

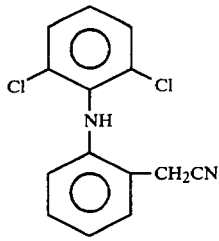

is not formed at all.

When the halogen is other than bromine or iodine, that is, when N,N-dimethyl-o-chlorophenylacetamide is used instead of the N,N-disubstituted-o-bromophenylacetamide or N,N-disubstituted-o-iodophenylacetamide, the intended condensate is obtained only in a low yield.

In view of the foregoing, the reaction of the present invention is Ulmann reaction in a broad sense, but occurrence of this reaction cannot be expected from the starting compound and it is considered that the reaction of the present invention is a peculiar reaction.

Various processes for the preparation of the novel compounds of the formula (I) will now be described.

Process A

The novel N,N-disubstituted-o-halogenophenylacetamide of the formula (I) that is used in the present invention is synthesized by reacting a commercially available o-halogenophenyl acetic acid represented by the following general formula (VI):

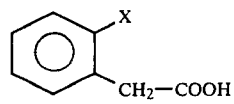 (VI)

wherein X stands for an iodine or bromine atom, with thionyl chloride to form an acid chloride and reacting the so formed acid chloride, as it is or after removal of the unreacted thionyl chloride or distillation under reduced pressure, with an amine compound represented by the following general formula (V):

 (V)

wherein $R_1$ and $R_2$ are as defined above.

The first stage reaction of the above preparation process is carried out in the absence of a solvent or the presence of an inert solvent at a reaction temperature of about 20 to about 80° C. for 30 minutes to 10 hours. The o-halogenophenylacetic acid/thionyl chloride molar ratio is in the range of from about 1/1 to about 1/10.

The second stage reaction is carried out at a temperature of about −5° to about 50° C. for 10 minutes to 10 hours in an organic solvent such as dichloromethane, benzene, toluene, chloroform, carbon tetrachloride, tetrachloroethane or carbon disulfide in a volume 3 to 10 times the volume of the reactants. The acid chloride/amine compound molar ratio is in the range from about 1/1 to about 1/10.

The amine compound of the formula (V) used for the preparation of the starting compound in the present invention is a secondary amine compound having lower alkyl groups as the substituents or a heterocyclic amine compound containing at least 2 nitrogen atoms (at least one of the nitrogen atoms may be replaced by an oxygen atom). As the lower alkyl group used herein is meant a linear or branched alkyl group having 1 to 6 carbon atoms. The hetercyclic amine compound preferably has up to 6 carbon atoms.

As the amine compound of the formula (V), there can be mentioned, for example, dimethyl amine, diethyl amine, di-n-propyl amine, di-idopropyl amine, di-n-butyl amine, di-isobutyl amine, di-n-hexyl amine, di-isohexylamine, methylethyl amine, methylpropyl amine, ethyl-n-butyl amine, pyrrolidine, piperidine, morpholine and piperazine.

When a gaseous amine compound, that is, dimethyl amine as the reactant, the reaction is carried out by blowing the gaseous amine into a solvent containing the acid chloride.

When a liquid amine compound is used as the reactant, the liquid amine compound is dropped in a solvent containing the acid chloride.

This reaction can be carried out also in an aqueous solution. More specifically, a solvent containing 10 to 50% by weight the acid chloride (for example, a benzene solution) is added dropwise to an aqueous solution of dimethyl amine containing 10% by weight of potassium hydroxide under violent agitation.

Process B

The N,N-disubstituted-o-halogenophenylacetamide derivative of the formula (I) can also be prepared by reacting a compound represented by the following general formula (IV):

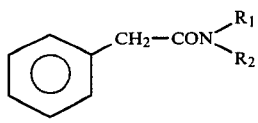 (IV)

wherein $R_1$ and $R_2$ are as defined above. with a halogen atom such as bromine or iodine in an appropriate solvent.

The N,N-disubstituted-phenylacetamide derivative of the formula (IV) is a commercially easily available known compound. Furthermore, this compound can be synthesized from commercially easily available phenylacetyl chloride or phenylacetic acid in the same manner as described above with respect to the process A for preparing the compound of the formula (I) from the o-halogenophenylacetic acid.

In this process halogenation is carried out by reacting the derivative of the formula (IV) with a halogen atom in an appropriate solvent. As the solvent, there can be used, for example, water, water containing 5 to 50% of an alcohol and water containing 10 to 50% of acetic acid. The use of water is especially preferred. The halogen atom is used in an amount of 1 to 10 moles per mole of the derivative of the formula (IV), preferably 2 to 4 moles per mole of the derivative of the formula (IV). The excessive halogen may be decomposed by sodium hydroxide, sodium bisulfite or the like. The reaction is carried out at a temperature of −5° to 50° C., preferably 10° to 30° C. The reaction is conducted for 2 to 48 hours, preferably 6 to 12 hours.

When the halogen atom is bromine, the resulting reaction mixture comprises as the main component about 75% of the o-bromo compound (N,N-di-substituted-o-bromophenylacetamide), and about 15% of the p-bromo compound (N,N-disubstituted-p-bromophenylacetamide) and about 10% of the unreacted starting N,N-disubstituted-phenylacetamide. The intended o-bromo compound can be purified and separated by distillation under reduced pressure.

It was found that the reactivity of the o-bromo compound to condensation with 2,6-dichloroaniline is much higher than that of the p-bromo compound. In other words, it was found that even if the p-bromo compound and the starting compund are present in the o-bromo compound, condensation of the o-bromo compound with 2,6-dichloroaniline is not substantially influenced. Namely, it is understood that a pure product of the o-bromo compound is not always used. More specifically, since the o-bromo compound is promptly reacted in the condensation reaction, the p-bromo compound and other compound are left in the reaction mixture in the unreacted state. After completion of the condensation reaction, the inorganic substance is removed by filtration and the solvent is removed by distillation under reduced pressure to obtain a crystal of the intended N,N-disubstituted-o-(2,6-dichloroanilino)-phenylacetamide. Since this crystal has ordinarily a very high purity, purification by recrystallization is ordinarily unnecessary. If desired, recrystallization may be performed by using a solvent such as methanol.

Process C

The N,N-disubstituted-o-halogenophenylacetamide of the formula (I) can also be prepared by reacting o-nitrophenylacetic acid with thionyl chloride to form a corresponding acid chloride (step i), removing the unreacted thionyl chloride from the reaction product mixture and reacting the acid chloride with an amine compound represented by the following general formula (V):

wherein $R_1$ and $R_2$ are as defined above, to form a compound represented by the following general formula (VII):

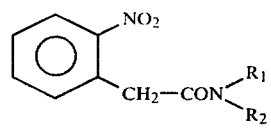

wherein $R_1$ and $R_2$ are as defined above, (step ii), reducing the nitro group of said compound to form an amino compund (step iii), and diazotizing the amino compound with nitrous acid and reacting the diazotized compound with potassium iodide or potassium bromide.

The reaction of the (step i) is carried out under the same conditions as described above with respect to the process for the preparation of the acid chloride. In order to improve the dissolving property of the starting compound, a solvent (in the dry state) such as benzene may be used.

At the (step ii), since the reactivity of the acid chloride used in this process with the amine compound is higher than that of the acid chlorides used in the above-mentioned processes, the reaction can be carried out under milder conditions. More specifically, the reaction may be carried out at a temperature of −5° to 10° C. for 10 minutes to 10 hours in a solvent such as benzene, toluene, xylene, dichloromethane, chloroform, methane tetrachloride or carbon disulfide in a volume 5 to 10 times the volume of the reactants. The acid chloride/amine compound molar ratio is from 1/1 to 1/10. The solvent for the acid chloride should be used in the dry state.

The amine compounds of the formula (V) such as mentioned above can be used in the anhydrous or hydrous state.

At the (step iii), reduction is carried out at room temperature according to the catalytic reduction method using a catalyst, for example, a palladiumcarbon catalyst in an amount of 1/100 to 1/50% by weight based on the nitro compound. The reaction pressure is in the range of atmospheric pressure to 150 atmospheres and the reaction time is in the range of from 30 minutes to 24 hours. As the solvent, ethanol, methanol, ethyl acetate or the like is used in a volume 5 to 20 times the volume of the reactant.

Any of known reduction methods may be used instead of the above-mentioned method.

The so obtained amino compound, that is, the N,N-disubstituted-o-aminophenylacetamide, is diazotized according to customary procedures. For example, the diazotization is carried out by adding an aqueous solution of nitrous acid having a concentration of about 25% to the amino compound in a 20% aqueous solution of $H_2SO_4$ at a reaction temperature of 0° to 5° C. over a period of 1 to 6 hours. The nitrous acid/amino compound molar ratio is in the range of 1.1/1 to 2.0/1.

The intended N,N-disubstituted-o-halogenophenylacetamide can be obtained by reacting the obtained diazotized compound with potassium iodide or potassium bromide. For example, the reaction is carried out by adding an aqueous solution of potassium iodide or potassium bromide to the diazotized compound over a period of 1 to 10 hours while maintaining the reaction temperature below 5° C. The amount used of potassium iodide or bromide is 1.1 to 5.0 moles per mole of the diazotized compound.

As will be apparent from the foregoing illustration, each of the above-mentioned preparation processes is industrially advantageous because the starting compound is cheap, the total step number is small, the yield of each step is high and the operation procedures are very simple.

The acid amide derivative of the formula (II) is obtained by practising the above-mentioned reaction of the first step of the present invention.

This acid amide derivative of the formula (II) is a very stable compound, and is characterized in that the derivative of the formula (II) has a very good crystallizing property and hence, purification can be accomplished very easily. More specifically, the acid amide derivative of the general formula (II) has a much higher melting point and a better crystallizing property than a corresponding organic acid ester represented by the following formula:

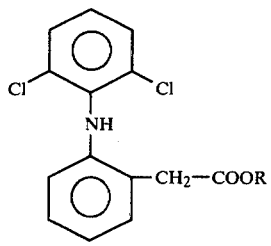

and hence, the acid amide derivative of the formula (II) can be purified very easily. These characteristic properties result in various advantages at the subsequent second step.

(2) Second Step:

At the second step, the N,N-disubstituted-o-(2,6-dichloroanilino)phenylacetamide derivative of the general formula (II) is hydrolyzed with an alkali to obtain the intended product (Diclofenac).

An alkali metal or alkaline earth metal hydroxide is preferably used as the alkali. From the industrial viewpoint, sodium hydroxide or potassium hydroxide is especially preferred.

The alkali is used in an amount of at least 1 mole, ordinarily 3 to 30 moles, per mole of the N,N-disubstituted-o-(2,6-dichloroanilino)phenylacetamide derivative. As the solvent for the hydrolysis there may be used water and inert organic solvent, for example, lower alcohols such as methanol, ethanol, propanol and butanol and ethers such as dioxane and methyl cellosolve. Aqueous mixtures containing such organic solvent at an optional ratio may also be used. A mixed solvent of water and a lower alcohol is especially preferred. The solvent is used in a volume 5 to 20times the volume of the reactants.

The hydrolysis is carried out at a temperature of about 50° to about 200° C., preferably 80° to 120° C.

When a low-boiling-point solvent is used, the hydrolysis is preferably carried out under reflux of the solvent, and when a high-boiling-point solvent is used, the hydrolysis is preferably carried out while maintaining the reaction temperature at 70° to 150° C.

The hydrolysis is completed within about 2 to about 50 hours. The termination of the reaction is confirmed, for example, by disappearance of spots of the compound of the formula (II) in thin layer chromatography. Thus, the intended compound of the present invention is obtained.

A sodium salt of Diclofenac is a white crystal having a decomposition point of 280° to 285° C. and has excellent analgesic, anti-inflammatory and antipyretic actions, and it can be broadly used for remedy of various acute and chronic inflammatory and pain diseases such as chronic articular rheumatics, arthritis deformans and common cold diseases.

The present invention will now be described in detail by reference to the following Examples that by no means limit the scope of the invention.

EXAMPLE 1

Preparation of N,N-dimethyl-o-iodophenylacetamide

In 100 ml of thionyl chloride was dissolved 72.0 g (0.275 mole) of o-iodophenylacetic acid, the reaction was carried out at an inner temperature of 50° C. for 1 hour under agitation and the mixture was refluxed for 30 minutes under agitation. After completion of the reaction, the unreacted thionyl chloride was removed by distillation under reduced pressure. Then, 30 ml of anhydrous benzene was added to the residue, and the solvent was removed by distillation under reduced pressure at an inner temperature of 40° C. Then, the residue was dissolved in 200 ml of anhydrous dichloromethane and the solution was added dropwise to 54.5 ml of a 50% aqueous solution of dimethyl amine under agitation at an inner temperature of 5° to 10° C. over a period of 20 minutes. Then, the reaction mixture was agitated for 1 hour at room temperature to complete the reaction. Then, 400 ml of water was added to the liquid reaction mixture, and the mixture was violently agitated and allowed to stand still to cause phase separation. The organic layer was washed with 2 times with 100 ml each of a 10% aqueous solution of hydrochloric acid, a 10% aqueous solution of sodium carbonate and a saturated aqueous solution of sodium chloride, and then dried with anhydrous sodium sulfate. The solvent was removed under reduced pressure and the residue was subjected to reduced pressure distillaton to obtain 75.5 g of a yellow oily product (solidified under cooling) having a boiling point of 140° to 142° C. under 0.6 mmHg. The yield was 95.0%.

Elementary analysis values: Found: H=4.31%, C=41.42%, N=4.62%; Calculated: H=4.19%, C=41.54%, N=4.84%.

Infrared absorption spectrum, $\nu CO$: 1640 $cm^{-1}$.

EXAMPLE 2

Preparation of N,N-diethyl-o-iodophenylacetamide

Procedures of Example 1 were repeated in the same manner except that a solution of 51.1 g of diethyl amine in 200 ml of anhydrous dichloromethane was used instead of dimethyl amine, to obtain N,N-diethyl-o-iodophenylacetamide as a yellow oily product having a boiling point of 148° to 149° C. under 1 mmHg in a yield of 96%.

Elementary analysis values as $C_{12}H_{16}NOI$: Found: C=45.44%, H=5.09%, N=4.42%; Calculated: C=45.21%, H=5.27%, N=4.61%.

Infrared absorption spectrum, $\nu CO$: 1640 $cm^{-1}$.

EXAMPLE 3

Preparation of N,N-dimethyl-o-iodophenylacetamide

To 10 g (0.038 mole) of o-iodophenylacetic acid was added 50 ml of a solution of 5.7 g (0.048 mole) of thionyl chloride in anhydrous benzene, and the mixture was refluxed for 2 hours under agitation. Then, the solvent and unreacted thionyl chloride were removed by distillation under reduced pressure below 40° C. and the residue was subjected to distillation under reduced pressure to obtain 9.6 g of o-iodophenylacetyl chloride as a light yellow oily product having a boiling point of 153° to 156° C. under 8 mmHg in a yield of 90%.

A solution of 7 g (0.025 mole) or o-iodophenylacetyl chloride in 25 ml of anhydrous benzene was added dropwise to a 50% aqueous solution of 5.6 g (0.062 mole) of dimethyl amine at 0° to 5° C. under violent agitation. The mixture was agitated at room temperature for 30 minutes, and the organic layer was separated, washed with water, a 10% aqueous solution of hydrochloric acid and a saturated aqueous solution of sodium chloride and dried with magnesium sulfate.

The solvent was removed by distillation under reduced pressure and the residue was subjected to distillation under reduced pressure to obtain 6.3 g of a light yellow oily product having a boiling point of 142° to 145° C. under 0.6 mmHg in a yield of 87.5%.

From results of the infrared absorption spectrum analysis, it was found that the product was the same as N,N-dimethyl-o-iodophenylacetamide obtained in Example 1.

EXAMPLE 4

In the same manner as described in Example 1, N,N-di-n-propyl-o-iodophenylacetamide having a boiling point of 153° to 154° C. under 0.4 mmHg was obtained in a yield of 94%.

Elementary analysis values as $C_{14}H_{20}NOI$: Calculated: C=48.71, H=5.84;, N=4.06%; Found: C=48.53%, H=5.96%, N=4.25%.

Infrared absorption spectrum, $\nu CO$: 1640 cm$^{-1}$.

EXAMPLE 5

In the same manner as described in Example 1, N,N-di-n-butyl-o-iodophenylacetamide having a boiling point of 176° to 177° C. under 0.3 mmHg was obtained in a yield of 97%.

Elementary analysis values as $C_{16}H_{24}NOI$: Calculated: C=51.48%, H=6.48%, N=3.75%; Found: C=51.35%, H=6.67%, N=3.54%.

Infrared absorption spectrum, $\nu CO$: 1640 cm$^{-1}$.

EXAMPLE 6

In the same manner as described in Example 1, N,N-di-n-hexyl-o-iodophenylacetamide having a boiling point of 204° to 205° C. under 0.25 mmHg was obtained in a yield of 90%.

Elementary analysis values as $C_{20}H_{32}NOI$: Calculated: C=55.94%, H=7.51%, N=3.26%; Found: C=55.78%, H=7.73%, N=3.27%.

Infrared absorption spectrum, $\nu CO$: 1641$^{-1}$.

EXAMPLE 7

(a) Preparation of N,N-dimethyl-o-nitrophenylacetamide

In a solution of 15 ml of thionyl chloride in 50 ml of anhydrous benzene was dissolved 18.1 g (0.1 mole) of o-nitrophenylacetic acid, and the solution was refluxed for 2 hours under agitation. After completion of the reaction, the solvent and unreacted thionyl chloride was removed by distillation under reduced pressure below 40° C. Then, 50 ml of anhydrous benzene was added to the residue and the resulting solution was subjected to distillation under reduced pressure below 40° C. Then, 100 ml of anhydrous benzene was added to the residue, and dry gaseous dimethyl amine was blown into the solution in an amount of about 0.25 mole under agitation at an inner temperature below 5° C. The reaction mixture was agitated at room temperature for 1 hour, and 100 ml of water was added and the mixture was further agitated. The organic layer was separated, washed with a 10% aqueous solution of hydrochloric acid, a 10% aqueous solution of sodium carbonate and a saturated aqueous solution of sodium chloride and dried with Glauber salt. The solvent was removed by distillation under reduced pressure and the residue was subjected to distillation under reduced pressure to obtain 17.1 g of a yellowish red oily product having a boiling point of 150° to 160° C. under 0.4 mmHg. The yield was 89%.

(b) Preparation of N,N-dimethyl-o-iodophenylacetamide

A 100 ml-capacity autoclave was charged with 5.0 g (0.026 mole) of N,N-dimethyl-o-nitrophenylacetamide, 0.5 g of 10%-palladium on carbon and 50 ml of 95% ethanol, and catalytic reduction was carried out under an initial pressure of 100 atmospheres at room temperature. The calculated amount of hydrogen was consumed within about 3 hours. The reaction was completed and the catalyst was removed by filtration. When the solvent was removed by distillation under reduced pressure, an amino compound having the nitro group reduced and converted to an amino group was quantitatively obtained in the form of a light-yellow crystal having a melting point of 68° to 70° C. (after recrystallization from methanol). The so obtained crude amino compound (4.1 g) was added to 17 ml of a 20% aqueous solution of $H_2SO_4$ and the inner temperature was lowered to 0° to 5° C. At the same temperature, a solution of 2.1 g (0.031 mole) of nitrous acid in 4 ml of water was added dropwise over a period of 30 minutes. Then, a solution of 5.2 g of potassium iodide in 7 ml of water was added dropwise at an inner temperature below 5° C. over a period of 30 minutes and the mixture was agitated for 1 hour at room temperature. After completion of the reaction, the precipitated oily product was extracted 3 times with 50 ml of benzene and the combined benzene extract was washed with a 10% aqueous solution of hypochlorite and with a saturated aqueous solution of sodium chloride, and was then dried with magnesium sulfate. The solvent was removed by distillation under reduced pressure and the residue was subjected to distillation under reduced pressure to obtain 4.5 g of a light yellow oily product having a boiling point of 140° to 145° C. under 0.6 mmHg in a yield of 62%. From results of the infrared absoption spectrum analysis and gas chromatography, it was found that the so obtained oily product was the same as N,N-dimethyl-o-iodophenylacetamide obtained in Example 1.

EXAMPLE 8

Preparation of N,N-dimethyl-o-bromophenylacetamide (i) o-Bromophenylacetyl chloride For 3 hours, 21 g (0.098 mole) of o-bromophenylacetic acid was refluxed in 100 ml of anhydrous benzene and 23.5 g (0.198 mole) of thionyl chloride. After completion of the reaction, benzene and unreacted thionyl chloride were removed by distillation under reduced pressure so that unreacted thionyl chloride was removed as completely as possible.

The residue was subjected to distillation under reduced pressure to obtain 21 g of a light yellow oily product having a boiling point of 98° to 99° C. under 0.6 mmHg. The yield was 91.86%.

(ii) N,N-dimethyl-o-bromophenylacetylamide

A solution of 21 g (0.0897 mole) of o-bromophenylacetyl chloride purified by distillation in 100 ml of anhydrous benzene was added dropwise to 50 ml of benzene and a 50% aqueous solution of dimethyl amine at 5° to 20° C. under violent agitation.

After completion of the reaction, the organic layer was separated and washed with a 10% aqueous solution of hydrochloric acid, a 10% aqueous solution of sodium hydroxide and a saturated aqueous solution of sodium chloride.

After drying with magnesium sulfate, the solvent was removed by distillation under reduced pressure and the residue was subjected to distillation under reduced pressure to obtain 21 g of a light yellow oily product (solidified under cooling) having a boiling point of 132° to 135° C. under 0.4 mmHg. The yield was 86.7%.

Elementary analysis values as $C_{10}H_{12}NOBr$: Found: C=49.83%, H=4.71%, N=5.57%; Calculated: C=49.61%, N=4.96%, N=5.78%.

(iii) N,N-dimethyl-o-(2,6-dichloroanilino)phenylacetamide

In 80 ml of xylene (having a boiling point of 138° to 141° C.), 8.5 g (0.0525 mole) of 2,6-dichloroaniline was refluxed together with 5.2 g (0.0215 mole) of N,N-dimethyl-o-bromophenylacetamide, 5.0 g (0.0357 mole) of potassium carbonate, 1.0 g of copper powder, 1.0 g of cuprous iodide and 2.0 g of sodium iodide for 48 hours under agitation, while water formed by the reaction was being separated. After completion of the reaction, the reaction mixture was treated with active carbon while it was still warm, and the filtrate was concentrated. The obtained residue was mixed with methyl alcohol and the crystal precipitated on cooling was recovered by filtration, washed with methyl alcohol and dried.

The filtrate was subjected to distillation under reduced pressure to recover 2,6-dichloroaniline having a boiling point of 80° to 82° C. Methyl alcohol was added to the residue and the crystal precipitated on cooling was recovered by filtration and combined with the above-mentioned crystal to obtain 5.7 g of a light pink crystal. The yield was 82.1%. Recrystallization from benzene gave a light pink prism having a melting point of 158° to 160° C.

From results of the infrared absorption spectrum analysis, nuclear magnetic resonance spectrum analysis and gas chromatography, it was found that the so obtained crystal was N,N-dimethyl-o-(2,6-dichloroanilino)phenylacetamide.

EXAMPLE 9

(i) N,N-dimethylphenylacetamide

In 204 ml of anhydrous benzene was dissolved 77.5 g (0.5 mole) of commercially available phenylacetyl chloride, and the solution was added dropwise to a 50% aqueous solution of 180 g (2.0 moles) of dimethyl amine, 50 g of ice and 100 ml of benzene at an inner temperature of 5° to 25° C. After completion of the dropwise addition, the mixture was agitated for 1 hour at the same temperature.

After completion of the reaction, the benzene layer was separated and the water layer was extracted 2 times with 100 ml of ethyl acetate.

The combined extract was washed 2 times with a saturated aqueous solution of sodium chloride and dried with magnesium sulfate, and the solvent was removed by distillation under reduced pressure. The residue was subjected to distillation under reduced pressure to obtain 74.3 g of a colorless oily product (solidified under cooling) having a boiling point of 110° to 112° C. under 0.4 mmHg. The yield was 91%.

(ii) Bromination of N,N-dimethylphenylacetamide

In 190 ml of water was dissolved 19 g (0.117 mole) of N,N-dimethylphenylacetamide (this amide is soluble in water). Then, 37.3 g (0.233 mole) of $Br_2$ was added dropwise to the solution at an inner temperature of 15° to 20° C. over a period of 10 minutes, and the mixture was agitated for 12 hours. Then, at the same temperature, 18.7 g (0.117 mole) of $Br_2$ was added dropwise to the mixture over a period of 10 minutes and the mixture was agitated for 6 hours. After completion of the reaction, sodium bisulfite was added to the reaction mixture and the mixture was agitated, whereby the color of the oily product precipitated in the lower portion was changed from red to light yellow.

Then, 50 ml of trichloromethane was added to the reaction mixture and the trichloromethane layer was separated, and the water layer was extracted 2 times with trichloromethane.

The combined trichloromethane extract was washed with a saturated aqueous solution of sodium chloride and dried with magnesium sulfate. The solvent was removed by distillation, and the residue was subjected to distillation under reduced pressure to obtain 28.5 g of a yellow oily product having a boiling point of 190° to 197° C. under 18 mmHg.

From comparison of results of gas chromatography of the so obtained product with results of gas chromatography of standard substances of N,N-dimethyl-o-bromophenylacetamide, N,N-dimethyl-p-bromophenylacetamide and starting N,N-dimethylphenylacetamide, it was found that the obtained product was a mixture comprising 69.83% of N,N-dimethyl-o-bromophenylacetamide, 16.52% of N,N-dimethyl-p-bromophenylacetamide and 13.64% of N,N-dimethylphenylacetamide.

Namely, the obtained product included 19.88 g of intended N,N-dimethyl-o-bromophenylacetamide, and the yield of the intended compound was 70.5%.

(iii) N,N-Dimethyl-o-(2,6-dichloroaniline)phenylacetamide

In 1400 ml of xylene (having a boiling point of 138° to 141° C.), 200 g of the starting material obtained in the same manner as described in (ii) of Example 9 (comprising 69% of N,N-dimethyl-o-bromophenylacetamide, 30.2% of N,N-dimethyl-p-bromophenylacetamide and 0.1% of N,N-dimethylphenylacetamide) was refluxed together with 218 g (1.346 moles) of 2,6-dichloroaniline), 80 g (0.571 mole) of potassium carbonate, 20 g of copper powder, 10 g of cuprous iodide powder and 10 g of sodium iodide under agitation for 66 hours while water formed by the reaction was being separated. After completion of the reaction, the reaction mixture was treated with active carbon while it was still hot. The solvent was removed by distillation under reduced pressure and the precipitated crystal was recovered by filtration under suction.

The recovered crystal was sufficiently washed with xylene to obtain 123.7 g of a light pink crystal of the same compound as N,N-dimethyl-o-(2,6-dichloroanilino)phenylacetamide obtained in (iii) of Example 8. The yield was 67.2%. The filtrate was subjected to distillation under reduced pressure to obtain 124 g (the recovery ratio being 85% of the theoretical value) of 2,6-dichloroaniline at a boiling point of 85° to 87° C. under 0.6 mmHg and 66.5 g of a lightly colored oily product at a boiling point of 140° to 160° C. under 0.6 mmHg. From results of gas chromatography, it was found that this oily product was a mixture comprising 41.2% of N,N-dimethyl-o-bromophenylacetamide, 55.2% of N,N-dimethyl-p-bromophenylacetamide and 3.6% of N,N-dimethylphenylacetamide. Thus, it was confirmed that 27.4 g (19.9%) of starting N,N-dimethyl-o-bromophenylacetamide was recovered in this oily product from 138 g of all of starting N,N-dimethyl-o-bromophenylacetamide. If the calculation was made while taking the amount recovered of starting N,N-dimethyl-o-bromophenylacetamide into account, it was seen that the yield of intended N,N-dimethyl-o-(2,6-dichloroanilino)phenylacetamide was 83.9%.

EXAMPLE 10

(i) A mixture of 11 g (0.0333 mole) of o-iodophenylacetomorpholide having a melting point of 92° to 93° C., 5.94 g (0.0367 mole) of 2,6-dichloroaniline, 5.14 g (0.0367 mole) of anhydrous potassium carbonate, 2.5 g of copper powder, 2.5 g of cuprous iodide and 160 ml of xylene having a boiling point of 138° to 141° C. was refluxed under agitation for 48 hours while water formed by the reaction was being separated. After completion of the reaction, the insoluble substance was removed by filtration while the reaction mixture was still hot, and the filtrate was treated with active carbon.

Then, the solvent was removed by distillation under reduced pressure, and 5 ml of methanol was added to the residue and the precipitated crystal was recovered by filtration under suction. The recovered crystal was recrystallized from methanol to obtain 11 g of a colorless needle of o-(2,6-dichloroanilino)phenylacetomorpholide having a melting point of 75° to 77° C. (after recrystallization from methanol). The yield was 90.4%.

Elementary analysis values as $C_{18}H_{18}N_2O_2Cl_2$: Calculated: H=4.97%, C=59.19%, N=7.67%; Found: H=4.72%, C=59.02%, N=7.78%.

Infrared absorption spectrum: 3250 cm$^{-1}$ ($\nu$NH), 1640 cm$^{-1}$ ($\nu$CO).

(ii) In 50 ml of n-butanol, 5.0 g of the condensate obtained in (i) above and 1.0 g of sodium hydroxide was refluxed under agitation for 6 hours. After completion of the reaction, the majority of the solvent was removed by distillation under reduced pressure. The residue was mixed with 50 ml of water and the solution was subjected to distillation under reduced pressure, and this operation was repeated 2 times so that n-butanol used as the solvent was removed as much as possible. The obtained crystal was recrystallized from water and treated with active carbon to obtain 3.8 g of a colorless scale having a decomposition point of 283° to 285° C. The yield was 87.0%. From results of the infrared absorption spectrum, nuclear magnetic resonance spectrum analysis and elementary analysis, it was found that the so obtained crystal was sodium o-(2,6-dichloroanilino)phenylacetate.

EXAMPLE 11

A mixture of 3.5 g (0.0123 mole) of o-bromophenylacetomorpholide having a boiling point of 180° to 181° C. under 0.4 mmHg and a melting point of 82° to 84° C., 4.0 g (0.0247 mole) of 2,6-dichloroaniline, 2.0 g (0.0143 mole) of anhydrous potassium carbonate, 0.5 g of copper powder, 0.5 g of cuprous bromide, and 1.0 g of sodium iodide was reacted in 100 ml of xylene for 96 hours. After completion of the reaction, the post treatment was carried out in the same manner as in Example 10 to obtain 3.73 g of a crystal having a melting point of 75° to 77° C. (after recrystallization from methanol), which was the same as o-(2,6-dichloroanilino)phenylacetomorpholide obtained in Example 10. The yield was 83%.

EXAMPLE 12

(i) A mixture of 4 g (0.0122 mole) of o-iodophenylacetopiperidine having a boiling point of 170° to 171° C. under 0.3 mmHg, 2.2 g (0.0136 mole) of 2,6-dichloroaniline, 1.85 g (0.0132 mole) of anhydrous potassium carbonate, 1.0 g of copper powder and 1.0 g of cuprous iodide was agitated in 100 ml of xylene under reflux for 48 hours, while water formed by the reaction was being separated.

After completion of the reaction, the insoluble substance was removed by filtration while the reaction mixture was still hot, and the filtrate was treated with active carbon. The solvent was removed by conducting distillation under reduced pressure 3 times and the residue was subjected to column chromatography using silica gel and benzene. Unreacted 2,6-dichloroaniline was recovered from the first fraction and a crystal of intended o-(2,6-dichloroanilino)phenylacetopiperidide was recovered from the second fraction. Recrystallization from methanol gave 4.21 g of a colorless needle having a melting point of 119° to 121° C. (after recrystallization from benzene). The yield was 95.1%.

Elementary analysis values as $C_{19}H_{20}Cl_2N_2O$: Calculated: H=5.55%, C=62.82%, N=7.71%; Found: H=5.47%, C=62.97%, N=7.66%.

Infrared absorption spectrum: 3210 cm$^{-1}$ ($\nu$NH), 1615 cm$^{-1}$ ($\nu$CO).

(ii) A mixture of 5.0 g of the condensate obtained in (i) above, 2.0 g of sodium hydroxide and 50 ml of n-butanol was heated and agitated for 10 hours. The post treatment was carried out in the same manner as described in (ii) of Example 10 to obtain intended sodium o-(2,6-dichloroanilino)phenylacetate.

EXAMPLE 13

(i) A mixture of 5.6 g (0.0199 mole) of o-bromophenylacetopiperidide having a boiling point of 201° to 202° C. under 1 mmHg, 4.1 g (0.0253 mole) of 2,6-dichloroaniline, 3.2 g (0.0229 mole) of anhydrous potassium carbonate, 1.5 g of copper powder, 1.5 g of cuprous bromide and 2.0 g of sodium iodide was reacted in 85 ml of xylene for 94 hours, and the post treatment was carried out in the same manner as described in (i) of Example 12 to obtain 4.1 g of o-(2,6-dichloroanilino)phenylpiperidide. The yield was 56%.

(ii) A mixture of 5.0 g of the condensate obtained in (i) above and 2.0 g of sodium hydroxide was heated and agitated in 50 ml of n-butanol for 10 hours. The post treatment was carried out in the same manner as described in (ii) of Example 10 to obtain intended sodium o-(2,6-dichloroanilino)phenylacetate.

EXAMPLE 14

(i) A mixture of 4.3 g (0.0137 mole) of o-iodophenylacetopyrrolidide having a boiling point of 170° to 171° C. under 0.3 mmHg, 4.5 g (0.0278 mole) of 2,6-dichloroaniline, 2.11 g (0.0151 mole) of anhydrous potassium carbonate, 1.0 g of copper powder and 1.0 g of cuprous iodide was agitated and refluxed in 100 ml of xylene for 22 hours, while water formed by the reaction was being separated. The post treatment was carried out in the same manner as described in (i) of Example 12 to obtain 4.2 g of intended o-(2,6-dichloroanilino)-phenylacetopyrrolidide in the form of a colorless needle having a melting point of 124° to 125° C. (after recrystallization from ethyl acetate). The yield was 87.9%.

Elementary analysis values as $C_{18}H_{18}N_2OCl_2$: Calculated: C=61.90%, H=5.19%, N=8.02%; Found: C=61.64%, H=5.08%, N=8.01%.

Infrared absorption spectrum: 3170 cm$^{-1}$ ($\nu$NH), 1620 cm$^{-1}$ ($\nu$CO).

(ii) A mixture of 5.0 g of the condensate obtained in (i) above and 2.0 g of soium hydroxide was heated and agitated in 50 ml of n-butanol for 10 hours, and the post treatment was carried out in the same manner as described in (ii) of Example 10 to obtain intended sodium o-(2,6-dichloroanilino)phenylacetate.

EXAMPLE 15

(i) A mixture of 5.4 g (0.02 mole) of o-bromophenylacetopyrrolidide having a boiling point of 170° to 171° C., 4.1 g (0.025 mole) of 2,6-dichloroaniline, 3.2 g (0.023 mole) of anhydrous potassium carbonate, 1.5 g of copper powder and 1.5 g of cuprous bromide was reacted in 85 ml of xylene for 92 hours to obtain 4.5 g of the same compound as o-(2,6-dichloroanilino) phenylacetopyrrolidide. The yield was 62%.

(ii) A mixture of 5.0 g of the condensate obtained in (i) above and 2.0 g of sodium hydroxide was heated and agitated in 50 ml of n-butanol for 10 hours. The post treatment was carried out in the same manner as described in (ii) of Example 10 to obtain intended sodium o-(2,6-dichloroanilino)phenylacetate.

EXAMPLE 16

(i) A mixture of 3.5 g (0.0095 mole) of N,N-di-n-butyl-o-iodophenylacetamide, 1.70 g (0.0105 mole) of 2,6-dichloroaniline, 1.46 g (0.0104 mole) of anhydrous potassium carbonate, 1.0 g of copper powder and 1.0 g of cuprous iodide was reacted in 53 ml of xylene for 45 hours. After completion of the reaction, the post treatment was carried out in the same manner as in Example 12 to obtain 3.14 g of N,N-di-n-butyl-o-(2,6-dichloroanilino)phenylacetamide in the form of a colorless needle having a melting point of 66° to 68° C. (after recrystallization from methanol).

Elementary analysis values as $C_{22}H_{28}N_2OCl_2$: Calculated: H=6.93%, C=64.86%, N=6.88%; Found: H=6.92%, C=64.62%, N=6.79%.

Infrared absorption spectrum: 3270 cm$^{-1}$ ($\nu$NH), 1630 cm$^{-1}$ ($\nu$CO).

(ii) A mixture of 5.0 g of the condensate obtained in (i) above and 2.0 g of sodium hydroxide was heated and agitated in 50 ml of n-butanol for 10 hours. The post treatment was carried out in the same manner as described in (ii) of Example 10 to obtain intended sodium o-(2,6-dichloroanilino)phenylacetate.

EXAMPLE 17

(i) A mixture of 4.1 g (0.012 mole) of N,N-di-n-propyl-o-iodophenylacetamide, 4.0 g (0.024 mole) of 2,6-dichlroaniline, 1.85 g (0.0132 mole) of anhydrous potassium carbonate, 1.0 g of copper powder and 1.0 g of cuprous iodide was reacted in 100 ml of xylene for 28 hours.

After completion of the reaction, the post treatment was carried out in the same manner as in Example 12 to obtain 3.92 g of N,N-dipropyl-o-(2,6-dichloroanilino)-phenylacetamide in the form of a colorless needle having a melting point of 84° to 86° C. (after recrystallization from methanol). The yield was 86.3%.

Elementary analysis values as $C_{20}H_{24}N_2OCl_2$: Calculated: H=6.38%, C=63.33%, N=7.38%; Found: H=6.35%, C=63.06%, N=7.38%.

Infrared absorption spectrum: 3270 cm$^{-1}$ ($\nu$NH), 1630 cm$^{-1}$ ($\nu$CO).

(ii) A mixture of 5.0 g of the condensate obtained in (i) above and 2.0 g of sodium hydroxide was heated and agitated in 50 ml of n-butanol for 10 hours. The post treatment was carried out in the same manner as described in (ii) of Example 10 to obtain intended sodium o-(2,6-dichloroanilino)phenylacetate.

EXAMPLE 18

(i) Preparation of N,N-dimethyl-o-(2,6-dichloroanilino)phenylacetamide

A mixture of 4.33 g (0.015 mole) of N,N-dimethyl-o-iodophenylacetamide, 5.03 g (0.031 mole) of 2,6-dichloroaniline, 1.62 g (0.0157 mole) of anhydrous potassium carbonate, 0.5 g of copper powder and 0.2 g of cuprous iodide was refluxed in 60 ml of toluene under agitation for 118 hours, while water formed by the reaction was being separated. After completion of the reaction, the insoluble substance was removed by filtration while the reaction mixture was still hot, and the filtrate was treated with active carbon. The solvent was removed by distillation under reduced pressure, and 10 ml of methanol was added to the residue and the precipitated crystal was recovered by filtration under suction. Recrystallization from benzene gave 4.2 g of colorless needle having a melting point of 156° to 158° C. The yield was 86.4%.

Infrared absorption spectrum: 3120 cm$^{-1}$ ($\nu$NH), 1620 cm$^{-1}$ ($\nu$CO).

Elementary analysis values Calculated: C=59.72, H=4.92, N=8.76; Found: C=59.46, H=4.99, N=8.76.

The methanol solution as the filtrate was combined with the filtrate left after recrystallization, and the solvent was removed by distillation under reduced pressure. The residue was subjected to column chromatography using silica gel and elution was carried out with benzene. Unreacted 2,6-dichloroaniline was obtained from the first fraction, 0.45 g (9.3%) of N,N-dimethyl-o-(2,6-dichlroanilino)phenylacetamide in the form of a colorless crystal having a melting point of 156° to 158° C. was obtained from the second fraction, and 0.012 g (2.7%) of starting N,N-dimethyl-o-iodophenylacetamide was recovered from the third fraction.

When calculation was made while taking the amount (2.7%) of the recovered starting material into account, it was found that the total yield of the intended compound was 98.4%.

(ii) Preparation of sodium o-(2,6-dichloroanilino)phenylacetate

A mixture of 1.0 g of N,N-dimethyl-o-(2,6-dichloroanilino)phenylacetamide, 2.0 g of sodium hydroxide and 15 ml of ethanol was heated under agitation for 5 hours. After completion of the reaction, the solvent was removed by distillation under reduced pressure. Then, 10 ml of water was added to the residual crystal and the crystal was dissolved by heating the mixture. Then, the solution was cooled to 5° C. and the precipitated crystal was recovered by filtration under suction. The crystal was recrystallized from 15 ml of water and the active carbon treatment was conducted. There was obtained 0.94 g of colorless scale having a decomposition point of 283° to 285° C. The yield was 95.7%.

The overall yield of sodium o-(2,6-dichloroanilino)phenylacetate from N,N-dimethyl-o-iodophenylacetamide through the above two steps (i) and (ii) was 94.2%.

EXAMPLE 19

(i) Preparation of N,N-methyl-o-(2,6-dichloroanilino)phenylacetamide

In 50 ml of anhydrous toluene was suspended 0.96 g of sodium hydride (containing 50% of mineral oil), and 3.24 g of 2,6-dichloroaniline was added to the suspension under agitation below 10° C. Then, the mixture was heated at 50° C. and agitated for 1 hour. Then, 2.88 g of N,N-dimethyl-o-iodophenylacetamide, 0.4 g of copper powder and 0.2 g of cuprous iodide were added, and the mixture was agitated under reflux for 24 hours. After completion of the reaction, the insoluble substance was removed by filtration, and the filtrate was concentrated under reduced pressure. Then, 5 ml of methanol was added to the residue and the mixture was cooled. The precipitated crystal was recovered by filtration.

Recrystallization from benzene gave 1.8 g of a colorless prism having a melting point of 156° to 158° C. The yield was 55.7%. From results of the infrared absorption spectrum analysis and mixed examination, it was found that the crystal was identical with N,N-dimethyl-o-(2,6-dichloroanilino)phenylacetamide.

(ii) Preparation of o-(2,6-dichloroanilino)phenylacetic acid

To 40 ml of a 15% ethanol solution of potassium hydroxide was added 1.7 g of N,N-dimethyl-o-(2,6-dichloroanilino)phenylacetamide, and the mixture was agitated under reflux for 4 hours. After completion of the reaction, the solvent was removed by distillation under reduced pressure, and 30 ml of water was added to the residue and the mixture was made acidic by hydrochloric acid at a temperature lower than 5° C. The precipitated crystal was recovered by filtration under suction, washed with water and dried. Recrystallization from a mixed solvent of ether and petroleum ether gave 1.45 g of a colorless crystal having a melting point of 158° to 160° C. The yield was 92.9%.

EXAMPLE 20

(i) Preparation of N,N-diethyl-o-(2,6-dichloroanilino)phenylacetamide

A mixture of 6.0 g (0.019 mole) of N,N-diethyl(o-iodophenyl)acetamide, 3.38 g (0.021 mole) of 2,6-dichloroaniline, 2.93 g (0.021 mole) of anhydrous potassium carbonate, 1.0 g of copper powder and 1.0 g of cuprous iodide was reacted in 85 ml of xylene for 24 hours to obtain 5.46 g of a colorless needle having a melting point of 99° to 101° C. The yield was 81.4%.

Infrared absorption spectrum: 3250 cm$^{-1}$ ($\nu$NH), 1630 cm$^{-1}$ ($\nu$CO).

Elementary analysis values as $C_{18}H_{20}Cl_2N_2O$: Found: C=61.81%, H=5.72%, N=8.03%; Calculated: C=61.55%, H=5.78%, N=7.97%.

(ii) A mixture of 5.0 g of the condensate obtained in (i) above and 2.0 g of sodium hydroxide was heated and agitated in 50 ml of n-butanol for 10 hours. The post treatment was carried out in the same manner as described in (ii) of Example 10 to obtain sodium o-(2,6-dichloroanilino)phenylacetate.

EXAMPLE 21

Preparation of N-methyl-N-[o-(2,6-dichloroanilino)phenylaceto]-piperidine

A mixture of 5.94 g (0.02 mole) of N-methyl-N'-(o-bromophenylaceto)piperidine, 3.2 g (0.020 mole) of 2,6-dichloroaniline, 3.2 g (0.022 mole) of anhydrous potassium carbonate, 1.6 g of cuprous bromide and 1.6 g of copper powder was reacted in 85 ml of xylene for 96 hours to obtain 2.5 g of a colorless needle having a melting point of 111° to 112° C. The yield was 33%.

Infrared absorption spectrum: 3200 cm$^{-1}$ ($\nu$NH), 1620 cm$^{-1}$ ($\nu$CO).

Elementary analysis values as $C_{19}H_{21}N_2OCl_2$: Found: C=60.58%, H=5.50%, N=11.14%; Calculated: C=60.33%, H=5.60%, N=11.10%.

EXAMPLE 22

Preparation of N-benzyl-N-methyl-o-(2,6-dichloroanilino)-phenylacetamide

A mixture of 10.0 g (0.031 mole) of N-benzyl-N-methyl-o-bromophenylacetamide having a boiling point of 202° to 203° C. under 0.5 mmHg, 6.1 g (0.037 mole) of 2,6-dichloroaniline, 5.2 g (0.037 mole) of anhydrous potassium carbonate, 2.6 g of cuprous bromide and 2.6 g of copper powder was reacted in 150 ml of xylene for 72 hours to obtain 7.5 g of a colorless needle having a melting point of 85° to 86° C. The yield was 56.0%.

Infrared absorption spectrum: 3200 cm$^{-1}$ ($\nu$NH), 1625 cm$^{-1}$ ($\nu$CO).

Elementary analysis values as $C_{22}H_{20}N_2OCl_2$: Found: C=66.21%, H=5.18%, N=6.88%; Calculated: C=66.16%, H=5.01%, N=7.02%.

EXAMPLE 23

Preparation of N-ethyl-N-phenyl-o-(2,6-dichloroanilino)phenylacetamide

A mixture of 6.36 g (0.02 mole) of N-ethyl-N-phenyl-(o-bromophenyl)acetamide having a boiling point of 185° to 190° C. under 2 mmHg, 6.48 g (0.04 mole) of 2,6-dichloroaniline, 3.0 g (0.02 mole) of anhydrous potassium carbonate, 2.0 g of copper powder and 2.0 g of cuprous bromide was reacted in 100 ml of xylene in the same manner as in Example 22 to obtain 6.1 g of a colorless prism having a melting point of 121° to 123° C. The yield was 77.4%.

Infrared absorption spectrum: 3200 cm$^{-1}$ ($\nu$NH), 1640 cm$^{-1}$ ($\nu$CO).

Elementary analysis values as $C_{22}H_{20}N_2OCl_2$:
Found: C=66.31%, H=5.24%, N=6.95%; Calculated: C=66.17%, H=5.01%, N=7.02%.

EXAMPLE 24

Preparation of N-methyl-N-phenyl-o-(2,6-dichloroanilino)-phenylacetamide

A mixture of 9.0 g (0.03 mole) of N-methyl-N-phenyl-(o-bromophenyl)acetamide having a boiling point of 174° to 180° C. under 2 mmHg, 9.7 g (0.06 mole) of 2,6-dichloroaniline, 4.1 g (0.029 mole) of anhydrous potassium carbonate, 2.0 g of copper powder and 2.0 g of cuprous bromide was reacted in 100 ml of xylene in the same manner as in Example 22 to obtain 8.2 g of a colorless prism having a melting point of 168° to 169° C. The yield was 72.1%.

Infrared absorption spectrum: 3200 cm$^{-1}$ ($\nu$NH), 1640 cm$^{-1}$ ($\nu$CO).

Elementary analysis values as $C_{21}H_{18}N_2OCl_2$:
Found: C=65.41%, H=4.48%, N=7.39%; Calculated: C=65.47%, H=4.71%, N=7.27%.

What is claimed is:

1. A process for the preparation of o-(2,6-dichloroanilino)phenylacetic acid or its pharmacologically acceptable acid addition salt, which comprises reacting an N,N-disubstituted-o-halogenophenylacetamide derivative represented by the following general formula (I):

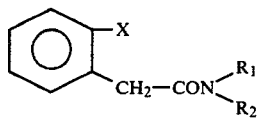
(I)

wherein $R_1$ and $R_2$, which may be the same or different, stand for a lower alkyl group, or one of $R_1$ and $R_2$ stands for a lower alkyl group and the other of $R_1$ and $R_2$ stands for a phenyl or benzyl group, or $R_1$ and $R_2$ are bonded together to form a heterocyclic ring together with a nitrogen atom and/or an oxygen atom, and X stands for an iodine or bromine atom,
with 2,6-dichloroaniline in the presence of a copper catalyst to form an N,N-disubstituted-o-(2,6-dichloroanilino)phenylacetamide represented by the following general formula (II):

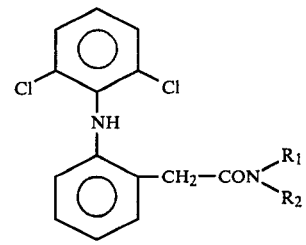
(II)

wherein $R_1$ and $R_2$ are as defined above, and hydrolyzing with an alkali.

2. A process for the preparation of N,N-disubstituted-o-(2,6-dichloroanilino)phenylacetamide derivatives represented by the following general formula (II):

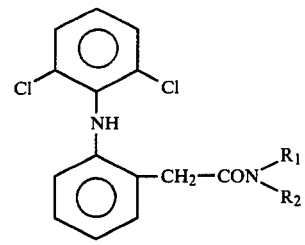
(II)

wherein $R_1$ and $R_2$, which may be the same or different, stand for a lower alkyl group, or one of $R_1$ and $R_2$ stands for a lower alkyl group and the other of $R_1$ and $R_2$ stands for a phenyl or benzyl group, or $R_1$ and $R_2$ are bonded together to form a heterocyclic ring together with a nitrogen atom and/or an oxygen atom,
which comprises reacting an N,N-diisubstituted-o-halogenophenylacetamide derivative represented by the following general formula (I):

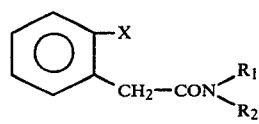
(I)

wherein $R_1$ and $R_2$ are as defined above, and X stands for an iodine or bromine atom, with 2,6-dichloroanline in the presence of a copper catalyst.

* * * * *